United States Patent [19]
Petrik

[11] Patent Number: 6,083,685
[45] Date of Patent: Jul. 4, 2000

[54] SYSTEMATIC EXTRACTION, AMPLIFICATION AND DETECTION OF RETROVIRAL SEQUENCES, AND OLIGONUCLEOTIDES FOR USE THEREIN

[75] Inventor: Juraj Petrik, Cambridge, United Kingdom

[73] Assignee: Cambridge University Technical Services Ltd., United Kingdom

[21] Appl. No.: 09/043,085
[22] PCT Filed: Sep. 6, 1996
[86] PCT No.: PCT/GB96/02196
§ 371 Date: Mar. 6, 1998
§ 102(e) Date: Mar. 6, 1998
[87] PCT Pub. No.: WO97/09452
PCT Pub. Date: Mar. 13, 1997

[30] Foreign Application Priority Data

Sep. 6, 1995 [GB] United Kingdom ................... 9518154

[51] Int. Cl.[7] ................ C12Q 1/70; C12Q 1/68; C12Q 1/04; C12Q 1/16; C07H 21/02

[52] U.S. Cl. ................... 435/5; 435/6; 435/34; 435/35; 536/23.1; 536/24.1; 536/24.3

[58] Field of Search ............... 435/5, 6, 34, 35; 536/23.1, 24.1, 24.3

[56] References Cited

PUBLICATIONS

Lower, et al., A General Method for the Identification of Transcibed Retrovirus Sequences (R–U5 PCR) Reveals the Expression of the Human Endogenous Retrovirus Loci HERV–H and HERV–K in Teratocarcinoma Cells, Virology 192, 501–511, see Materials and Method, 1993.

Xiong, Y., Eickbush, T.H. (1990) Origin and evolution of retroelements based upon their reverse transcriptase sequences, The EMBO Journal. 9(10): 3353–3362.

*Primary Examiner*—Hankyel Park
*Attorney, Agent, or Firm*—Saliwanchik, Lloyd & Saliwanchik

[57] ABSTRACT

A method for determining the presence of retroviral RNA or DNA in a sample comprises using one or more detectable oligonucleotides that each hybridise with the primer binding site of a retroviral genome or its complement.

10 Claims, 1 Drawing Sheet

Fig. 1

SEQUENCE LISTING (1) GENERAL INFORMATION:

(iii) NUMBER OF SEQUENCES: 58

(2) INFORMATION FOR SEQ ID NO: 1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Olignucleotide"

(xi) SEQUENCE DESCRIPTION: SEQ ID NO: 1:

ATCCCGGACG AGCCCCCA                                              18

(2) INFORMATION FOR SEQ ID NO: 2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 2:

GTCCCTGTTC GGGCGCCA                                              18

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 3:

CTCCTGGCTG GCTCACCA                                              18

(2) INFORMATION FOR SEQ ID NO: 4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 4:

AACCGGGCGG AAACACCA                                              18

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 5:

CGAATCCCAC CGCTGCCA                                                            18

(2) INFORMATION FOR SEQ ID NO: 6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 6:

TGCCCGCATT CTCCACCA                                                            18

(2) INFORMATION FOR SEQ ID NO: 7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 7:

ATCCTGCCGA CTACGCCA                                                            18

(2) INFORMATION FOR SEQ ID NO: 8:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 8:

TCCCGGGTTT CGGCACCA                                                            18

(2) INFORMATION FOR SEQ ID NO: 9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 9:

CCTTGTCTCT TAGGCCCA                                                            18

(2) INFORMATION FOR SEQ ID NO: 10:

(i) SEQUENCE CHARACTERISTICS:
            (A) LENGTH: 18 base pairs
            (B) TYPE: nucleic acid
            (C) STRANDEDNESS: single (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 10:

TTCCGGCTCG AAGGACCA                                                  18

(2) INFORMATION FOR SEQ ID NO: 11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 11:

TTCCCGGGCG GCGCACCA                                                  18

(2) INFORMATION FOR SEQ ID NO: 12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 12:

TTCCCGGCCA ATGCACCA                                                  18

(2) INFORMATION FOR SEQ ID NO: 13:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 13:

ATCTCGGTGG GACCTCCA                                                  18

(2) INFORMATION FOR SEQ ID NO: 14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(xi) SEQUENCE DESCRIPTION: SEQ ID NO: 14:

TCCTCACACG GGGCACCA                                                  18

(2) INFORMATION FOR SEQ ID NO: 15:

(i) SEQUENCE CHARACTERISTICS:
            (A) LENGTH: 18 base pairs
            (B) TYPE: nucleic acid

```
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 15:

GCCCAYCCAG GGACGCCA                                                 18

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 16:

TCCCACTTCT GACACCCA                                                 18

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 17:

ATCYGAGTCA CRGCACCA                                                 18

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 18:

GCCCCACGTT GGGCGCCA                                                 18

(2) INFORMATION FOR SEQ ID NO: 19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 19:

AACCATCCTC TGCTACCA                                                 18

(2) INFORMATION FOR SEQ ID NO: 20:

(i) SEQUENCE CHARACTERISTICS:
        (A) LENGTH: 18 base pairs
```

(B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 20:

ATCACGTCGG GGTCACCA                                                   18

(2) INFORMATION FOR SEQ ID NO: 21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 21:

TACTCAACGG CACCGCCA                                                   18

(2) INFORMATION FOR SEQ ID NO: 22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 22:

ATCCCCGGAC GGGAGCCA                                                   18

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 23:

TTCCCCGACG GGGAGCCA                                                   18

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 24:

CTCCCGGTGT GGGAACCA                                                   18

(2) INFORMATION FOR SEQ ID NO: 25:

(i) SEQUENCE CHARACTERISTICS:

```
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 25:

TGGGGGCTCG TCCGGGAT                                                  18

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 26:

TGGCGCCCGA ACAGGGAC                                                  18

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 27:

TGGTGAGCCA GCCAGGAG                                                  18

(2) INFORMATION FOR SEQ ID NO: 28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 28:

TGGTGTTTCC GCCCGGTT                                                  18

(2) INFORMATION FOR SEQ ID NO: 29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 29:

TGGCAGCGGT GGGATTCG                                                  18

(2) INFORMATION FOR SEQ ID NO: 30:
```

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 30:

TGGTGGAGAA TGCGGGCA                                                    18

(2) INFORMATION FOR SEQ ID NO: 31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 31:

TGGCGTAGTC GGCAGGAT                                                    18

(2) INFORMATION FOR SEQ ID NO: 32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 32:

TGGTGCCGAA ACCCGGGA                                                    18

(2) INFORMATION FOR SEQ ID NO: 33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 33:

TGGGCCTAAG AGACAAGG                                                    18

(2) INFORMATION FOR SEQ ID NO: 34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 34:

TGGTCCTTCG AGCCGGAA                                                    18

(2) INFORMATION FOR SEQ ID NO: 35:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 35:

TGGTGCGCCG CCCGGGAA                                              18

(2) INFORMATION FOR SEQ ID NO: 36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 36:

TGGTGCATTG GCCGGGAA                                              18

(2) INFORMATION FOR SEQ ID NO: 37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 37:

TGGAGGTCCC ACCGAGAT                                              18

(2) INFORMATION FOR SEQ ID NO: 38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 38:

TGGTGCCCCG TGTGAGGA                                              18

(2) INFORMATION FOR SEQ ID NO: 39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 39:

TGGCGTCCCT GGRTGGGC                                              18
```

(2) INFORMATION FOR SEQ ID NO: 40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 40:

TGGGTGTCAG AAGTGGGA                                      18

(2) INFORMATION FOR SEQ ID NO: 41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 41:

TGGTGCYGTG ACTCRGAT                                      18

(2) INFORMATION FOR SEQ ID NO: 42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 42:

TGGCGCCCAA CGTGGGGC                                      18

(2) INFORMATION FOR SEQ ID NO: 43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 43:

TGGTAGCAGA GGATGGTT                                      18

(2) INFORMATION FOR SEQ ID NO: 44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 44:

TGGTGACCCC GACGTGAT                                      18

(2) INFORMATION FOR SEQ ID NO: 45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 45:

TGGCGGTGCC GTTGAGTA                                      18

(2) INFORMATION FOR SEQ ID NO: 46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 46:

TGGCTCCCGT CCGGGGAT                                      18

(2) INFORMATION FOR SEQ ID NO: 47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 47:

TGGCTCCCCG TCGGGGAA                                      18

(2) INFORMATION FOR SEQ ID NO: 48:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 48:

TGGTTCCCAC ACCGGGAG                                      18

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide"

(xi) SEQUENCE DESCRIPTION: SEQ ID NO: 49:

CARAANCCRT TNGCNARRTC                                   20

(2) INFORMATION FOR SEQ ID NO: 50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION:   /desc = "Oligonucleotide"

(xi) SEQUENCE DESCRIPTION: SEQ ID NO: 50:

AARAANGCRT CNKTNARRTC                                                          20

(2) INFORMATION FOR SEQ ID NO: 51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION:   /desc = "Oligonucleotide"

(xi) SEQUENCE DESCRIPTION: SEQ ID NO: 51:

AARAANGCRT CNCGNARRTC                                                          20

(2) INFORMATION FOR SEQ ID NO: 52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION:   /desc = "Oligonucleotide"

(xi) SEQUENCE DESCRIPTION: SEQ ID NO: 52:

AARAANCANT CRTKNANRTC                                                          20

(2) INFORMATION FOR SEQ ID NO: 53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION:   /desc = "Oligonucleotide"

(xi) SEQUENCE DESCRIPTION: SEQ ID NO: 53:

WARTANGCRT CNCCNAYRTC                                                          20

(2) INFORMATION FOR SEQ ID NO: 54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION:   /desc = "Oligonucleotide"

(xi) SEQUENCE DESCRIPTION: SEQ ID NO: 54:

-continued

```
CCYTGNGGNA GNYKNNTCCA                                               20

(2) INFORMATION FOR SEQ ID NO: 55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 55:

CSNTGNGGNA GNMMNNTCCA                                               20

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 56:

CCKTGNGGNA GNACNTTRWG                                               20

(2) INFORMATION FOR SEQ ID NO: 57:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 57:

NRNANRTCRT CNAYRTA                                                  17

(2) INFORMATION FOR SEQ ID NO: 58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 58:

CTNNTNGAYA CNGGNGC                                                  17
```

SYSTEMATIC EXTRACTION, AMPLIFICATION AND DETECTION OF RETROVIRAL SEQUENCES, AND OLIGONUCLEOTIDES FOR USE THEREIN

FIELD OF THE INVENTION

This invention relates to oligonucleotides and their use, especially in extraction, amplification and assay procedures.

BACKGROUND OF THE INVENTION

As well as exogenous retroviruses such as Human Immunodeficiency Viruses (HIV 1 and 2) which cause AIDS and Human T-Cell Leukaemia Viruses (ATLV/HTLV I and II), a cause of adult T-cell leukaemia and Tropical Spastic Paraparesis, there is also a large group of endogenous retroviruses (ERVs). Exogenous viruses undergo all stages of the replication cycle, including the production of the next generation of infectious viral particles, and can spread horizontally. Endogenous retroviruses are in fact DNA copies of the viral genome integrated into host DNA as a result of a germ line infection which may have occurred many millions years ago, and they are transmitted vertically. Most ERVs are apparently inactive as documented by their identical localisation in the genomes of humans and some primates. Some are present in one or a few copies, more frequently in hundreds, sometimes in thousands or more copies. However, they are not the only representatives of so called repetitive sequences in mammalian genomes. As much as 10% of the mouse and human genomes appear to consist of the products of reverse transcription, such as processed pseudogenes, SINEs, LINEs, Puppys and ERVs. In the human genome, ERVs can account for 0.1–0.6%.

There is an increasing body of evidence that repetitive sequences are not simply junk DNA. Human endogenous retroviruses (HERVS) have been implicated in oncogenesis but also in autoimmune disorders. HERVs may interfere with normal cellular functions in several ways. Although the vast majority of the HERV coding sequences are interrupted by stop codons and thus cannot produce functional proteins, if transcribed they may recombine, eventually producing infectious virus.

A large proportion of the human genome consists of different variable repetitive sequences. Its study is extremely difficult. To date, apart from incidental findings of the HERV sequences in the process of sequencing other genes, the majority of HERVs have been identified by low-stringency hybridisation using exogenous retroviral genome-derived probes. This method, however, can detect only closely-related sequences.

The most conserved region of retroviral genomes is the primer binding site (PBS). Specific PBS-derived oligonucleotides, or part of tRNA itself, have been used as hybridisation probes or primers in a primer extension reaction (Kroger et al (1987) J. Virol. 61:2071–5).

Another highly conserved region is the coding region for reverse transcriptase (RT). Some domains are conserved, not only among retroviruses, but also among other retroelements (Xiong et al (1990) EMBO J. 9:3353–62).

The polymerase chain reaction (PCR) has been successfully used to amplify a fragment between two conserved domains of RT using primers specific for certain groups of retroviruses (Shih et al (1989) J. Virol. 63:64–75). Another conserved sequence used for PCR is that of a protease gene. These amplification methods have their limitations, in that two sets of degenerate primers have to be used, and the amount of sequence information obtained is mostly limited to short regions of the RT gene.

There are some 1300 tRNA genes and pseudogenes in the human genome coding for some 60–90 tRNAs of which 20 have been sequenced so far. Some 11 tRNAs have been so far described to prime minus DNA strand synthesis in all retroviruses. Of those 7 are used by human exo- and endogenous retroviruses (see Table 1).

WO-A-9603528 discloses certain oligonucleotides for use in screening.

SUMMARY OF THE INVENTION

This invention describes a procedure for the rapid and systematic analysis of retroviral sequences. It is especially useful for the endogenous retroviral (ERV) sequences which cannot be systematically studied by other means. In addition, this method can be used to search for new exo- or endogenous retroviruses as it does not require previous knowledge of the sequence. Examples of template preparation and amplification of the retroviral RNA and DNA are shown, depending on the aim of the analysis. The described procedure is automatable and suitable for analysis of large sets of samples if desired, such as samples from patients with leukemias or other neoplasias as compared to control samples. Other potential application areas are large sequencing projects where ERVs can serve as useful tags, animal evolutionary studies and breeding programmes and, possibly, forensic science. For use, kits may be provided including primers and capture oligonucleotides described in this invention.

More specifically, according to the present invention, a method for determining the presence of retroviral RNA or DNA in a sample, comprises using one or more detectable oligonucleotides that each hybridise with the primer binding site of a retroviral genome or its complement.

DESCRIPTION OF THE INVENTION

In one aspect of the invention, 24 oligonucleotides identical to the last 18 3'-end nucleotides of various human transfer RNA (tRNA), or mammalian tRNAs which are indistinguishable from human ones (see FIG. 1), can be used in the following manner: Conjugated to a capture moiety such as biotin, they can specifically capture the genomic RNA or RNA transcripts of exogenous and endogenous retroviruses (ERV) including recombinant viruses, from whole blood, serum or plasma, blood cells, cell lines and various tissues. More generally, probes of the invention are detectable; this means that they may carry a detectable label, or their presence may be detected by any suitable means, at any stage.

Figure 1:
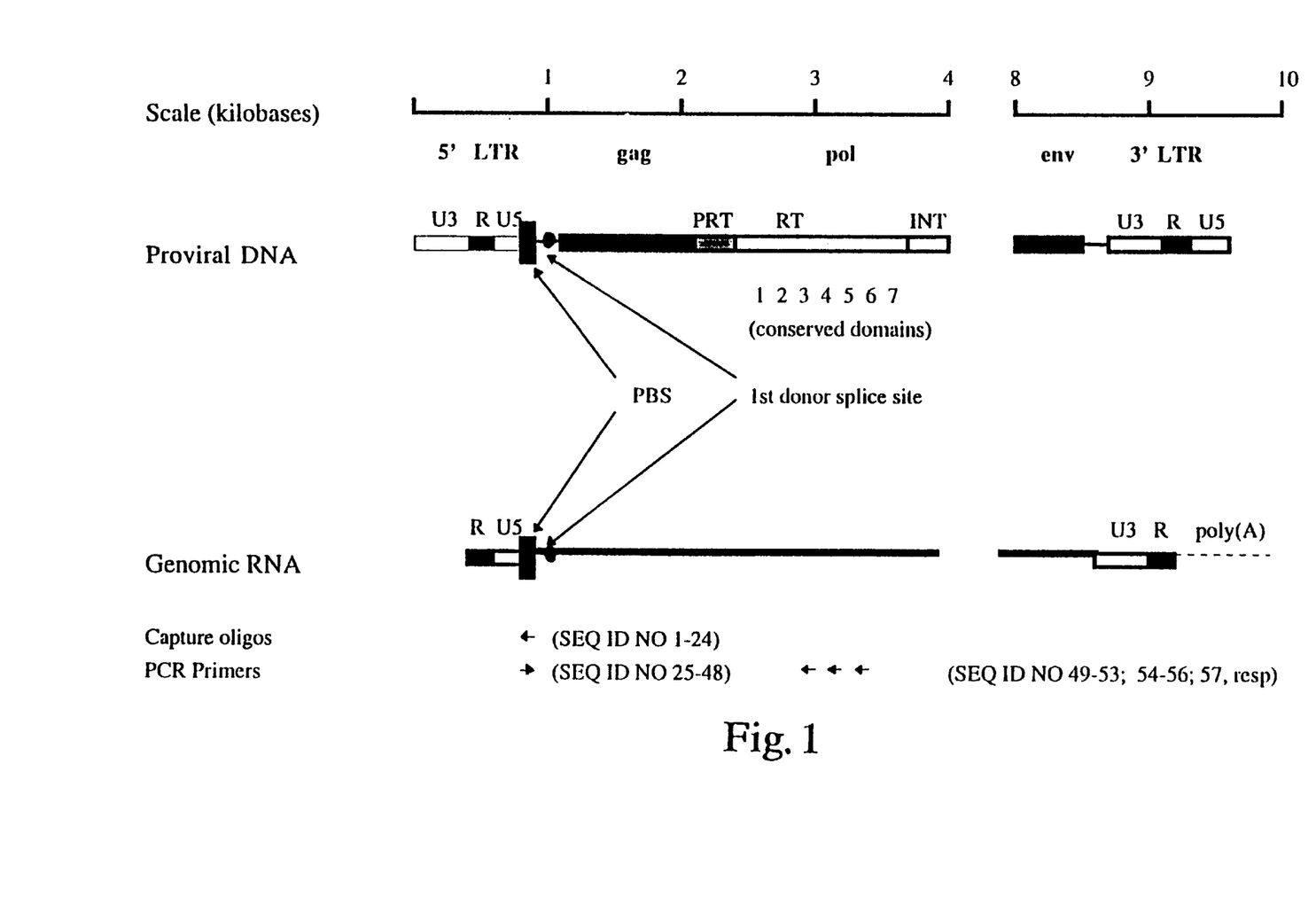
FIG. 1 is a map showing the positions of capture oligonucleotides and PCR primers on the proviral DNA and genomic RNA of retroviruses. It should be considered in connection with Table 1.

These probes can be used separately, in groups (e.g. 4–6 or more) or all together. By using capture probes derived from tRNAs which have not been yet described to prime any human retrovirus (FIG. 1) one can, in principle, select for RNAs of novel human retroviral sequences. These oligonucleotides (see also SEQ ID Nos. 1–24) are:

| | | | | |
|---|---|---|---|---|
| tRNA Proline | ATC CCG GAC GAG CCC CCA | | PBS Proline | TGG GGG CTC GTC CGG GAT |
| tRNA Lysine 3 | GTC CCT GTT CGG GCG CCA | | PBS Lysine 3 | TGG CGC CCG AAC AGG GAC |
| tRNA Arginine | CTC CTG GCT GGC TCA CCA | | PBS Arginine | TGG TGA GCC AGC CAG GAG |
| tRNA Valine | AAC CGG GCG GAA ACA CCA | | PBS Valine | TGG TGT TTC CGC CCG GTT |
| tRNA Leucine (a) | CGA ATC CCA CCG CTG CCA | | PBS Leucine (a) | TGG CAG CGG TGG GAT TCG |
| tRNA Alanine | TGC CCG CAT TCT CCA CCA | | PBS Alanine | TGG TGG AGA ATG CGG GCA |
| tRNA Serine | ATC CTG CCG ACT ACG CCA | | PBS Serine | TGG CGT AGT CGG CAG GAT |
| tRNA Phenylalanine (GAA) | TCC CGG GTT TCG GCA CCA | | PBS Phenylalanine (GAA) | TGG TGC CGA AAC CCG GGA |
| tRNA Phenylalanine (ATA) | CCT TGT CTC TTA GGC CCA | | PBS Phenylalanine (ATA) | TGG GCC TAA GAG ACA AGG |
| tRNA Tyrosine 1,2 | TTC CGG CTC GAA GGA CCA | | PBS Tyrosine 1,2 | TGG TCC TTC GAG CCG AAA |
| tRNA Glycine (CCC) | TTC CCG GGC GGC GCA CCA | | PBS Glycine (CCC) | TGG TGC GCC GCC CGG GAA |
| tRNA Glycine (GCC) | TTC CCG GCC AAT GCA CCA | | PBS Glycine (GCC) | TGG TGC ATT GGC CGG GAA |
| tRNA Glutamine | ATC TCG GTG GGA CCT CCA | | PBS Glutamine | TGG AGG TCC CAC CGA GAT |
| tRNA Methionine (a) | TCC TCA CAC GGG GCA CCA | | PBS Methionine (a) | TGG TGC CCC GTG TGA GGA |
| tRNA Asparagine | GCC CAC/TCCAGGG ACG CCA | | PBS Asparagine | TGG CGT CCC TGGG/ATGGGC |
| tRNA Leucine (b) | TCC CAC TTC TGA CAC CCA | | PBS Leucine (b) | TGG GTG TCA GAA GTG GGA |
| tRNA Histidine | ATC T/CGAGTCACG/AGCACCA | | PBS Histidine | TGG TGCC/TGTGAC TCA/GGAT |
| tRNA Lysine 1,2 | GCC CCA CGT TGG GCG CCA | | PBS Lysine 1,2 | TGG CGC CCA ACG TGG GGC |
| tRNA Methionine (b) | AAC CAT CCT CTG CTA CCA | | PBS Methionine (b) | TGG TAG CAG AGG ATG GTT |
| tRNA Tryptophan | ATC ACG TCG GGG TCA CCA | | PBS Tryptophan | TGG TGA CCC CGA CGT GAT |
| tRNA Aspartic acid (a) | TAC TCA ACG GCA CCG CCA | | PBS Aspartic acid (a) | TGG CGG TGC CGT TGA GTA |
| tRNA Aspartic acid (b) | ATC CCC GGA CGG GAG CCA | | PBS Aspartic acid (b) | TGG CTC CCG TCC GGG GAT |
| tRNA Aspartic acid (c) | TTC CCC GAC GGG GAG CCA | | PBS Aspartic acid (c) | TGG CTC CCC GTC GGG GAA |
| tRNA Glutamic acid | CTC CCG GTG TGG GAA CCA | | PBS Glutamic acid | TGG TTC CCA CAC CGG GAG |

SEQ ID Nos. 1 and 2 are disclosed in WO-A-9603528 (incorporated herein by reference), for the specific extraction of RNAs of HIV and HTLV viruses, respectively.

A second aspect of the invention lies in the use of labelled (radioactively or non-radioactively, e.g. biotinylated) oligos described above (SEQ ID Nos. 1–24) as probes for hybridization to Northern blots (RNA separated according to size in agarose gel electrophoresis, transferred and fixed to nitro-cellulose or nylon membranes). This application is useful for rapid analysis of the presence of particular sequences in RNA samples, as it provides additional information on size of hybridising bands, and also for comparative qualitative and quantitative studies using control vs. patients' RNA preparations. For the detection of hybridising sequences, commercially-available kits detecting biotin-labelled molecules can be used.

In a third aspect of the invention, unambiguously defined PBS-derived primers (SEQ ID No 25–48) are used for the systematic amplification of the retroviral sequences in ordered combinations with a limited number of antisense primers derived from other conserved parts of retroviral genome (protease, reverse transcriptase; see FIG. 1). In this case, however, PBS primers are complementary (not identical) to the last 18 nucleotides of various tRNAs (see above; this means that some are identical to PBS sequences described in various exo- and endogenous viruses. Many are not yet known, and are "potential" PBS sequences (see Table 1). The combinations including these "potential" PBS sequences should select for novel retroviral sequences.

Primers of the second set (antisense primers) are complementary to conserved domains of reverse transcriptase (domains 1–7) and protease. They are degenerate, so that a few primers from a particular domain (in fact only one in domain 5) can be used for amplification of all or most of known retroviral sequences.

The sense PBS primers are identical to PBS which are complementary to the last 18 nucleotides of tRNAs described as primers for exogenous and endogenous human retroviruses, but also those derived from last 18 nucleotides of human tRNAs not yet described to prime retroviruses. These sense primers (see also SEQ ID Nos. 25–48) are reverse complements of the above anti-PBS capture oligonucleotides and are shown in the same order:

Examples of antisense primers are shown below. A limited number of primers derived from particular conserved regions can amplify existing known exo- and endogenous retroviruses. Other conserved region(s) of retroviral genome can be used to design similar sets of primers. The conserved domains of RT are numbered according to Xiong et al, supra.

Primers described in the third aspect of the invention or other primers derived from conserved regions of the RT or protease genes can be double-labelled with reporter and quencher fluorophores using Taqman technology (Perkin-Elmer). These labelled probes have to be positioned internally in respect of PCR primers. When added to the reaction, the signal is created only when the target sequence is amplified. This can not only confirm that using a particular combination of primers yields the amplified product without analysing it on the gel, but using group-specific antisense primers labelled with various reporter fluorophores (differing in emitting wavelengths) can directly classify amplified sequence.

Specific antisense primers (see also SEQ ID Nos. 49–57) are:

| | |
|---|---|
| Domain 3 RT | CAA/G AAI CCA/G TTI GCI AA/GA/G TC |
| Domain 3 RT | AAA/G AAI CCA/G TCI T/GTI AA/GA/G TC |
| Domain 3 RT | AAA/G AAI GCA/G TCI CGI AA/GA/G TC |
| Domain 3 RT | AAA/G AAI CAI TCT/C TT/GI AIA/G TC |
| Domain 3 RT | A/TAA/G TAI GCA/G TCI CCI AT/CA/G TC |
| Domain 4 RT | CCT/C TGI GGI AGI T/CG/TI ITC CA |
| Domain 4 RT | CG/CI TGI GGI AGI C/AC/AI ITC CA |
| Domain 4 RT | CCT/G TGI GGI AGI ACI TTA/G T/AG |
| Domain 5 RT | IA/GI AIA/G TCA/G TCI AC/TA/G TA |

An example of a single probe derived from the conserved domain of protease gene is (see also SEQ ID No. 58):

protease probe CTI ITI GAT/C ACI GGI GC

If used at the same time for classification, the primers from domain 3 RT (SEQ ID Nos. 49–53) can be used as probes if primers from domain 4 (SEQ ID Nos. 54–56) or primer from domain 5 (SEQ ID No. 57) are used as antisense PCR primers. Similarly, primers from domain 4 (SEQ ID Nos. 54–56) can be used as probes if primer from domain 5 (SEQ ID No. 57) is used as antisense PCR primer etc.

The template for PCR can be either selectively extracted RNA as described in the first aspect of the invention (RT PCR) or cellular genomic DNA, depending on the purpose of the investigation.

In a further aspect of the invention, the labelled (radioactively or non-radioactively, e.g. biotinylated) tRNA-derived and/or RT-derived oligos can be used to screen genomic and cDNA libraries prepared from various sources (DNA, RNA from normal cells, specific cell lines, patients, samples etc.). Clones hybridising to both probes are increasingly likely to contain retroviral sequences and those hybridising to tRNA-derived oligos from tRNAs not known to prime retroviruses are likely to contain novel retroviral sequences. The advantage of this approach is that a positive clone can be directly used for sequencing or a probe preparation as it is already cloned.

The selective extraction of retroviral RNAs together with the use of defined combinations of two sets of PCR primers derived from the most conserved regions of a retroviral genome greatly simplifies the study of endogenous retroviruses, by-passing the problem of high complexity, and introducing a systematic approach. This approach can be combined with detection technology (such as Taqman) which does not require post-PCR processing and can, potentially, detect simultaneously several differently labelled probes in one reaction. Such a set-up provides an automatable procedure for rapid analysis of retroviral sequences in any sample. In fact, using the method of simultaneous RNA extraction described for HCV in WO-A-9603528, one can analyse up to 60 samples at a time.

The selective RNA extraction can eliminate many problems observed with the RT PCR using a total RNA as a template. Non-specific amplification may not only produce unwanted background sequences but may sometimes completely obscure targeted sequence. This is particularly important for simultaneous amplification and detection of several target sequences (multiplex PCR) where non-specific amplification can severely interfere with interpretation of the result. Specific capture may eliminate this problem, and it can at the same time represent the first step of the systematic amplification procedure, reducing the number of necessary combinations of the two primer sets. In a comparison of RT PCR on total RNA and captured RNA, the latter provided better results (not shown).

Anti-PBS biotinylated capture oligonucleotides can be used for screening of particular cDNA or genomic libraries, for the detection and capture of the specific clones. To increase the probability that a hybridising clone contains retroviral sequence, the filters can be re-hybridised with labelled oligos from conserved parts of RT or protease gene.

The use of biotinylated anti-PBS primers as tools for rapid detection and transcription pattern analysis of retroviral transcripts is based on an observation that, in a vast majority of retroviral genomes, the first splice donor site is located downstream of PBS (see FIG. 1), and PBS becomes part of the leader sequence present in the majority if not all RNA transcripts. As mentioned, it can be a very useful approach for comparative qualitative and quantitative studies. Preliminary experiments showed an expected hybridisation pattern using control Northern blots prepared on RNA extracted from cells infected with known viruses. Hybridisation of $^{32}$P-labelled oligo corresponding to 3'-end of tRNA Lysine 3 known to prime HIV 1 and 2 (SEQ ID No. 2) to the total and poly (A)+ RNA from uninfected and HIV1-infected CEM cells showed some non-specific hybridisation on total RNA from uninfected cells; in mRNA fractions, only poly (A)+ from infected cells showed a hybridisation signal corresponding to several mRNA species.

Perhaps the most important aspect of the invention is the systematic method of amplification of retroviral sequences. The method of this invention uses only one set of degenerate primers derived mainly from conserved regions of RT. The specificity is introduced through the unambiguously defined PBS-derived primers. Ordered combination of PBS-derived and RT-derived primers can be used to amplify most existing retroviral sequences, in a systematic manner.

The technique has been verified using DNA and RNA from cells infected with HIV and HTLV viruses. The reaction conditions have been optimised in respect of non-degenerate:degenerate primer ratio (optimal ratio 1:6), annealing temperature etc. The specific products have been confirmed by hybridisation to virus-specific labelled probes prepared from the corresponding cloned viral genomes. The size of expected PCR products for various retrovirus is between 2.0 and 3.5 kilobase (including gag, protease and major part of RT gene). The amplified HTLV I and HIV 1 PCR products were close to 2.1 and 2.3 kb when using antisense primers from domains 3 (SEQ ID No. 50 and 53, respectively) and 5 (SEQ ID No. 57) of the reverse transcriptase, and corresponding PBS-derived primers (SEQ ID Nos. 25 and 25, respectively).

If the aim is to look for retroviral sequences (e.g. HERV sequences) which are transcriptionally active, then the template should be RNA as explained earlier. The conditions have been established (see Examples, 1.3.) for the successful RT PCR using captured RNA and primers from two sets (sense; SEQ ID Nos. 25–48; and antisense, SEQ ID Nos. 49–57).

The following Examples illustrate the invention.

1 Retroviral RNA Analysis 1.1. Retroviral RNA Capture When plasma or serum samples are analysed the RNA can be directly captured with biotinylated anti-PBS oligonucleotides (SEQ ID Nos. 1–24) and streptavidin coated paramagnetic particles (SPMP), starting with 1.1.3. The analysis of intracellular RNA works well when a total RNA is first extracted (1.1.1.) followed by the removal of small RNA molecules by LiCl precipitation (1.1.2.). The LiCl precipitation and the capture procedure should be preceded by a short denaturation to remove any annealed natural primer tRNA molecules which could interfere with a capture.

1.1.1. Total RNA Extraction

RNA from 1–5×10$^7$ cells {peripheral blood mononuclear cells (PBMC) or subfractions; control cell lines uninfected or infected with HIV, HTLV (CEM, CEM/HIV, MT2, 1010 etc.)} was extracted using Rnazol B (AMS Biotechnology (Europe) Ltd.) according to manufacturers, instructions. After precipitation and centrifugation the RNA pellet was washed with 80% ethanol, dried and dissolved in 200 μl of DEPC-treated water.

1.1.2. LiCl Precipitation

Total RNA is denatured (60–88° C. for 12–4 min), placed on ice and the same volume of 4 M LiCl is added. After an overnight incubation at 4° C. and centrifugation the high-molecular weight RNA pellet is dissolved in 140 μl of DEPC-treated water.

1.1.3. Capture from Total RNA 24 biotinylated capture oligonucleotides (SEQ ID Nos. 1–24) can be used simultaneously, in groups or individually. 20–100 μl of SPMPs (Promega) are used per oligo per sample. SPMPs are concentrated using a magnetic stand and resuspended in 6×SSC (standard saline citrate). 20–100 pMoles of each capture oligo per sample is added and incubated with SPMPs for 10 minutes with shaking. Unbound capture oligo(s) is removed by SPMP concentrating and two washing steps with 1×SSC. After an additional wash with 5×binding buffer (0.05 M Tris-Cl, pH 7.4; 2.5 M LiCl; 0.01 M EDTA), the SPMP-oligo(s) complex is resuspended at 40 μl per sample of 5xbinding buffer and 20 μl of loxlysis buffer (0.1 M Tris-Cl, pH 7.4; 1.4 M NaCl; 0.05 M KCl; 10% Triton X-100) is added. This mixture is mixed with 140 μl of RNA from the previous step (1.1.2.) and incubated at 37° C. for 1 hour with constant shaking. After two washing steps with 1xSSC, the captured RNA is eluted into a small volume (15–100 μl) of DEPC-treated water at 60–88° C. for 10–4 minutes, ready for further analysis.

1.1.4. Direct capture $1-5\times10^7$ cells are resuspended in 400 μl of 1.25xlysis buffer (as in 1.1.3. but containing in addition 0.5% SDS) by pipetting up and down. Subsequently 100 μl of SPMPs in 5xbinding buffer, linked to desired number of capture oligos (prepared as in 1.1.3.) were added and incubated at 37° C. for 20–60 minutes with constant shaking. SPMPs were washed twice with 1xSSC and RNA eluted into small volume of DEPC-treated water as in 1.1.3.

1.2. Retroviral RNA Analysis by Hybridisation

This technique is designed for a fast comparative analysis of the presence of active (transcribed) retroviral sequences. As mentioned above the PBS-derived sequence becomes a part of retroviral transcripts. Total or captured RNA separated on agarose-formaldehyde gels and transferred to a membrane (Northern blotting) is hybridised to labelled (e.g. biotinylated) anti-PBS oligos (such as SEQ ID Nos. 1–24).

RNA electrophoresis and Northern blotting are according to standard protocols. Prehybridisation (1 hour) and hybridisation (3 hours) were in 5xSSC; 5xDenhardt solution; 0.5% SDS in hybridisation oven (Hybaid) at 50–55° C., followed by four 5-minute washings: two with 2xSSC/0.5% SDS and two with 0.5xSSC/0.5% SDS.

Biotin detection kits such as chemiluminiscent Phototope (NEB) can be used for visualisation. The membrane(s) can be stripped and re-probed.

1.3. Retroviral RNA Analysis by RT-PCR

Several protocols of RT-PCR were evaluated. Generally, the hot start is a prerequisite as the PBS-derived primers tend to produce non-specific background products. Some protocols included separate cDNA and amplification steps, using AmpliTaq Gold for the latter for "invisible" hot start. This enzyme limited the PBS oligos from self-priming.

A one-tube protocol of XL RNA PCR kit (Perkin Elmer) produced satisfactory results. The following protocol was used for the RNA captured from MT2 and 1010 cells (containing HTLV I) with a group of four capture oligos including HTLV-specific tRNA Pro-derived oligo: cDNA reaction: 25 pmoles of SEQ ID Nos. 57; Mn++ final concentration 1.8 mM; other components according to manufacturers' instructions.

Programme: 88° C./4 min (only RNA and a primer in water); 57° C./75 min (the rest of the components added); 94° C./1 min.

Amplification: Mg++ is at 1.5 mM; 25 pMoles of a sense primer (SEQ ID No. 25) was added; other components according to manufacturers' instruction; 20 cycles: ramp 55° C. to 65° C. for 1min 45 sec 94° C. for 25 sec; 20 cycles: as above, with autoextension 15 sec.

All PCR reactions were carried-out on PCR system 9600. Among the positive and negative controls were reactions containing only one of the primers, mainly because of the potential of self-priming of PBS-derived primers.

The amplification can be combined with detection using Taqman technology. The inclusion of double-labelled Taqman m probe(s) can serve two purposes: to monitor the presence or absence of amplifiable retroviral sequence in particular sample or using particular primer combinations; to type amplified retroviral sequence if using type-specific Taqman probes in multiplex amplification.

2. Retroviral DNA Analysis 2.1. DNA Extraction

Cellular DNA can be prepared by numerous adequate techniques. Standard proteinase K method was used.

2.2. Systematic Retroviral DNA Amplification 0.1–1.0 μg DNA was used in 50 μl PCR reaction. Hot-start technique was used throughout the experiments. The optimal ratio of non-degenerate (PBS-derived; SEQ ID Nos. 25–48) to degenerate (RT-derived; SEQ ID Nos. 49–57) primers was found to be 1:6. The ordered combinations of these two groups of primers were investigated.

Programme of typical PCR reaction was: 98° C./5 min; 47–57° C. (depending on primer)/45 sec; followed by 30–35 cycles consisting of: 72° C./2min 30 sec, 94° C./30 sec, 7–57° C./45 sec; and a final extension 7 min at 72° C.

To confirm the specificity of control reactions, Southern blotting and hybridisation to specific probes were carried out using standard techniques. The PCR products of supposedly unknown origin were cloned, sequenced and analysed. A semi-nested PCR using an internal antisense primer was sometimes used to confirm retroviral origin of the amplified product.

3. Systematic Selection of Clones Containing Retroviral Sequences from the Genomic and cDNA Libraries Plaques or colonies of genomic and cDNA libraries were transferred to nylon membranes, fixed and hybridised using standard techniques. $^{32}$P- or biotin-labelled oligos (SEQ ID 1–24 and 49–57) were used for hybridisation as described in 1.2. Positive clones from high-density screening were re-screened at lower density. DNA from individual clones was used for further analysis by PCR and sequencing.

TABLE 1

| SEQ ID NO | Derived from tRNA | Known to prime exo- or endogenous retroviruses | Known to prime human exo- or endogenous retroviruses |
|---|---|---|---|
| 1 | Proline | + | + |
| 2 | Lysine 3 | + | + |
| 3 | Arginine | − | + |
| 4 | Valine | − | − |
| 5 | Leucine (a) | − | − |
| 6 | Alanine | − | − |
| 7 | Serine | − | − |
| 8 | Phenylalanine (GAA) | + | − |
| 9 | Phenylalanine (ATA) | + | − |
| 10 | Tyrosine 1,2 | − | − |
| 11 | Glycine (CCC) | + | − |
| 12 | Glycine (GCC) | + | − |
| 13 | Glutamine | + | − |
| 14 | Methionine (a) | − | − |
| 15 | Asparagine | − | − |
| 16 | Leucine (b) | − | − |
| 17 | Histidine | − | + |
| 18 | Lysine 1,2 | + | + |
| 19 | Methionine (b) | − | − |
| 20 | Tryptophan | + | − |
| 21 | Aspartic acid (a) | − | − |
| 22 | Aspartic acid (b) | − | − |
| 23 | Aspartic Acid (c) | − | − |
| 24 | Glutamic acid | + | + |

I claim:

1. A method for determining the presence of retroviral RNA or DNA in a sample, which comprises using one or more first detectable oligonucleotides that each hybridise with the primer binding site of a retroviral genome or its complement, and one or more further detectable oligonucleotides that each hybridise to a conserved region of the retroviral genome or the complement thereof, other than the primer binding site or its complement, wherein the one or more further oligonucleotides can hybridise to different retroviral genomes.

2. A method according to claim 1, wherein the or each first oligonucleotide has any one of the sequences defined as SEQ ID Nos. 1–48.

3. The method according to claim 1, wherein the or each further oligonucleotide has any of the sequences defined as SEQ ID Nos. 49–58.

4. The method according to claim 1, wherein the or each further oligonucleotide is used for amplification.

5. The method according to claim 1, which comprises using, as a set, all or substantially all of the first oligonucleotides having the sequences defined as SEQ ID Nos. 25–48, in combination with one of said further detectable oligonucleotides, and then with one or more others of said further detectable oligonucleotides that hybridise to different domains of said conserved region.

6. The method according to claim 1, wherein at least one of first or further the oligonucleotides is labelled or linked to a capture moiety.

7. The method according to claim 1, wherein the sample is a genomic DNA or cDNA library.

8. The method according to claim 1, wherein the sample has been taken from a mammalian subject.

9. A method for detecting a new retrovirus, said method comprising detecting an oligonucleotide having any one of the sequences defined as SEQ ID Nos. 5–17, 19–23, 28–41 and 43–47 hyridized to a retroviral genome, or the complement thereof, of said retrovirus.

10. The method according to claim 8, wherein said sample is selected from the group consisting of blood, serum, plasma, blood cells, cell lines and tissue.

* * * * *